(12) United States Patent
Grote et al.

(10) Patent No.: US 7,807,617 B2
(45) Date of Patent: *Oct. 5, 2010

(54) PEPTIDE INHIBITORS OF TOXINS DERIVED FROM LL-37

(75) Inventors: Johannes Jakobus Grote, Zoeterwoude (NL); Jan Wouter Drijfhout, Leiden (NL)

(73) Assignee: Academisch Ziekenhuis Leiden, Leiden (NL)

( * ) Notice: Subject to any disclaimer, the term of this patent is extended or adjusted under 35 U.S.C. 154(b) by 548 days.

This patent is subject to a terminal disclaimer.

(21) Appl. No.: 10/543,521

(22) PCT Filed: Jan. 27, 2004

(86) PCT No.: PCT/NL2004/000060

§ 371 (c)(1), (2), (4) Date: Apr. 5, 2006

(87) PCT Pub. No.: WO2004/067563

PCT Pub. Date: Aug. 12, 2004

(65) Prior Publication Data

US 2006/0223755 A1     Oct. 5, 2006

(30) Foreign Application Priority Data

Jan. 28, 2003   (EP)  .................... 03075274

(51) Int. Cl.
*C07K 14/00* (2006.01)
(52) U.S. Cl. .......................... 514/1; 530/300
(58) Field of Classification Search ................. 530/300; 514/2
See application file for complete search history.

(56) References Cited

U.S. PATENT DOCUMENTS 6,040,291 A * 3/2000 Hirata ..................... 514/12
6,103,888 A * 8/2000 Larrick et al. ............. 536/23.5

FOREIGN PATENT DOCUMENTS

EP    0955312 A    11/1999

OTHER PUBLICATIONS

Gennaro et al. 2000; Structural features and biological activities of the cathelicidin-derived antimicrobial peptides. Biopoly 55: 31-49.*
Sawa et al. 1998; Evaluation of antimicrobial and lipolysaccharide-neutralizing effects of a synthetic CAP18 fragment against *Pseudomonas aeruginosa* in a mouse model. Antimicrobial AGnents and Chemotherapy 42(12): 3269-3275.*
Gutsmann, E.A., et al., "Interaction of CAP18-derived peptides with membranes made from endotoxins or phospholipids", *Biophysical Journal* 2001, 80:2935-2945.
Kirikae, T., et al., "Protective effects of a human 18-kilodalton cationic antimicrobial protein (CAP18)-derived peptide against murine endotoxemia", *Infection and Immunity*, United States 1998, 66(5):1861-1868.
Nagaoka, Isao, et al., "Augmentation of the lipopolysaccharide-neutralizing activities of human cathelicidin CAP18/LL-37-derived antimicrobial peptides by replacement with hydrophobic and cationic amino acid residues", *Clinical and Diagnostic Laboratory Immunology* 2002, 9(5):972-982.

* cited by examiner

*Primary Examiner*—Karen Cochrane Carlson
(74) *Attorney, Agent, or Firm*—Hoffmann & Baron, LLP

(57) ABSTRACT

The invention relates to a peptidic compound with affinity to bacterial and fungal toxins, especially to lipopolysaccharide or lipoteichoic acid. The peptidic compound includes an amino acid sequence $X_1KEFX_2RIVX_3RIKX_4FLRX_5LVX_6$, wherein $X_1$ represents the N-terminal part; $X_2$ is K or E; $X_3$ is Q or E; $X_4$ is D or R; $X_5$ is N or E; $X_6$ represents the C-terminal part; an amino acid of the core sequence is optionally derivatized; the N-terminal part is acetylated, and/or the C-terminal part is amidated, and/or the sequence differs from the native amino sequence $X_1KEFKRIVQRIKDFLRNLVX_6$.

11 Claims, No Drawings

PEPTIDE INHIBITORS OF TOXINS DERIVED FROM LL-37

This application is the U.S. National Phase of International Application Number PCT/NL2004/000060 filed on 27 Jan. 2004, which is incorporated herein by reference.

This application asserts priority to European Application No. 03075274.5 filed on Jan. 28, 2003. The disclosure of European Application No. 03075274.5 is hereby incorporated by reference.

FIELD OF THE INVENTION

The invention relates to compounds which have affinity for toxins and especially for fungal and bacterial toxins such as lipopolysaccharide (LPS) or lipoteichoic acid (LTA), and which can inhibit or neutralize such toxins. In addition, the present invention relates to methods for the preparation of such compounds, their therapeutic and diagnostic use, compositions comprising the compounds, genetic material encoding them, and methods for their administration.

BACKGROUND OF THE INVENTION

Modern pharmacotherapy has been extremely successful in fighting microbial, and especially bacterial, infections, which used to be one of the prime causes of premature death until the middle of the last century. More recently, however, growing concerns over the wide-spread use of highly effective antibiotics have arisen because of the steady increase of bacterial resistance. In fact, over the past 25 years, antibiotic resistance—especially multiple resistance to a broad range of antibiotic compounds—has increased in virtually every species of bacteria examined. It is presently believed that the antibacterial agents of the most advanced type, which are unaffected by common resistance mechanisms, are the compounds which use appears to select for multidrug-resistant mutants.

Based on this development, experts recommend to use antibiotics far more restrictively than in the past, both in agriculture and in human medicine. For instance, minor infections—especially those which are not even typically caused by bacteria, such as the common cold—should not be treated with antibiotics, which should rather be reserved for more serious conditions. Furthermore, it is necessary to develop novel compounds for treating bacterial infections with completely different types of pharmacological activity, preferably with some activity which is independent from bacterial resistance to common antibiotics.

One of the conditions in which the widespread use of antibiotics has been discussed controversially is otitis media, either in its acute form or in its chronic state. It has been shown that the number of patients with otitis media with effusion (OME), i.e. a type of otitis characterized by the presence of fluid in the middle ear without the symptoms of an acute infection, has increased dramatically after the introduction of antibiotic therapy for early acute otitis media (AOM), suggesting that the antibiotics themselves play a part in OME (Lim et al., Laryngoscope 92, 278-286, 1982). It is believed that antibiotics like penicillin interfere with the development of local immune responses, such as with the production of local IgM in the middle ear (Howie et al., Ann. Otol. Rhinol. Laryngol. 85 Suppl. 25, 18-19, 1976). Another disadvantage of antibiotic therapy is that the bacteria are killed, but their toxins are still active.

It has been suggested that, for the treatment of these and other conditions resulting from bacterial or fungal infection, it may be advantageous to use compounds which do not kill the microorganisms or germs themselves, but rather neutralize their toxins and allow the natural host defense mechanisms to control the spread of the infection (Nell, The Role of Endotoxin in the Pathogenesis of Otitis Media With Effusion, PhD Thesis, Leiden, 1999). At the same time, this strategy would support the rapid restoration of impaired mucosal functions.

A major role among microbial toxins, such as fungal toxins and especially bacterial toxins, involved in a number of infectious conditions such as otitis is played by endotoxins, a group of lipopolysaccharides (LPS) found in the cell wall of gram-negative bacteria, consisting of a polysaccharide conjugated with a highly toxic lipid moiety, lipid A. One of the recent therapeutic approaches to treat OME is to administer compounds that neutralize endotoxin, or LPS (Nell, ibid.).

Various compounds capable of neutralizing endotoxin, or LPS, are presently known. For instance, several anti-endotoxin antibodies have been developed, such as HA-1A and E5, a human and a mural monoclonal IgM antibody, respectively. These antibodies have been shown to improve survival rates of patients with some severe conditions such as septic shock (Ziegler et al., New Engl. J. Med. 324, 429-436, 1991). However, their activity and specificity is considered unsatisfactory.

Another group of substances active against endotoxin is derived from a human endogenous protein termed bacterial permeability-increasing protein (BPI), which is stored in the azurophilic granules of neutrophils (Gazzano-Santoro et al., Infection and Immunity 60:11, 4754-4761, 1992). BPI, which is a strongly cationic protein, not only neutralizes free endotoxins, but also inhibits or kills bacteria cells per se by increasing the permeability of their outer membranes. BPI is indeed a potent, natural antibiotic, induced by the presence of LPS and some other triggers including tumor necrosis factor (TNF). However, most of its activity is associated with the immune cells synthesizing it, i.e. polymorphonuclear macrophages.

Several recombinant proteins derived from BPI have also been developed, such as $rBPI_{23}$ (Kohn et al., 1993) and $rBPI_{21}$ (Horwitz et al., 1996), which largely represent the N-terminal portions of BPI with molecular weights of 23 and 21 kDa, respectively. The use of BPI and BPI-derived compounds in the treatment of OME has, e.g., been described in WO-A-00/71149.

Another family of natural compounds with antimicrobial activity are the cathelicidins, a class of peptides produced by respiratory epithelial cells, alveolar macrophages, and other tissues. In their native forms, these compounds are linear, α-helical, cystein-free peptides or proteins. Cathelicidins are cationic and comprise a highly conserved signal sequence and pro-region, cathelin. However, their C-terminal domain encoding the mature peptide shows substantial heterogeneity. The peptides may have 12 to 80 amino acids.

The most prominent human cathelicidin is an 18 kDa cationic antimicrobial protein, CAP18. The 37 C-terminal amino acids of CAP18, i.e. peptide LL-37, represent a domain responsible for the high affinity and neutralizing capacity for LPS (Sawa et al., Antimicr. Agents Chemother. 42:12, 3269-3275, 1998). Several truncated peptides derived from CAP18 or LL-37 have been developed and tested, such as those disclosed by Sawa (Sawa et al., ibid.), Gutsmann (Gutsmann et al., Biophys. J. 80, 2935-2945, 2001), and in U.S. Pat. No. 6,040,291 and its European counterpart EP-A-0 955 312.

Further, reference is made to an article of Nagaoka Isao et al. in Clinical and Diagnostic Laboratory Immunology 9 (5)

(2002) 972-982 and an article of Kirikae et al. in Infection and Immunity 66 (5) (1998), 1861-1868.

Nagaoka et al. describe the aminoacid sequence of LL-37 and the 18-mer $K^{15}$-$V^{32}$ derived therefrom, whereas Kirikae et al. focus on a number of CAP-18 derived patents.

Truncated peptides derived from LL-37 in which the native aminoacid sequence is preserved, and especially such peptides comprising the aminoacid sequence KEFKRIVQRIKDFLRNLV (SEQ ID NO: 1) are hence described in the prior art.

In general, relatively small peptides are preferred over proteins such as CAP18 as lead candidates for therapeutical compounds for several reasons. Firstly, they can more easily be optimized, adapted, and modified to conserve or augment their desired activity and specificity. Secondly, they are easier to obtain or synthesize, and therefore more accessible. Thirdly, they are easier to formulate and deliver, as proteins are often unstable and not bioavailable after non-parenteral administration.

OBJECTS OF THE INVENTION

Despite the efforts in the prior art, there is a need for further peptides and peptidic compounds which have LPS- and LTA-neutralizing activity and may serve as pharmaceutical agents or leads for the development of novel pharmaceutical agents for treating bacterially induced diseases and conditions, such as otitis.

Further, there is a continuing need for such compounds having no or little undesirable inflammatory activity, such as stimulation of cytokine production, T-cell proliferation, activation of extracellular signal-related kinases (ERK), or chemotaxis of neutrophils, all of which are part of the activity spectrum of the presently known CAP18-derived peptides.

One of the main objects of the invention is to provide novel compounds which have affinity and neutralization capability for microbial toxins, and especially fungal and bacterial toxins such as lipopolysaccharides (LPS) and lipoteichoic acid (LTA), but which at the same time have reduced inflammatory activity.

It is a further object to adapt the known native amino acid sequence derived from LL-37 (and CAP-18) in such a way that the affinity and neutralization or inhibition functions is maintained in about the same order of magnitude or even improved, while at the same time the stability of the peptides is optimized.

Other objects are to provide methods for preparing such compounds, as well as therapeutic and diagnostic methods and compositions.

These and other objects of the present invention will become clear on the basis of the following description.

SUMMARY OF THE INVENTION

In a first aspect, the present invention provides compounds with affinity to lipopolysaccharides (LPS) or lipoteichoic acid (LTA). The compounds are peptidic in their chemical nature and comprise an amino acid sequence $X_1KEFX_2RIVX_3RIKX_4FLRX_5LVX_6$ (SEQ ID NO: 2) (herein-below, also referred to as core (amino acid) sequence), wherein $X_1$ represents the N-terminal part of the sequence, $X_2$ is K or E, $X_3$ is Q or E, $X_4$ is D or R, $X_5$ is N or E, and $X_6$ represents the C-terminal part; wherein one or more of the amino acids of the core sequence may be derivatized; wherein the N-terminal part is acetylated and/or the C-terminal part is amidated and/or the amino acid sequence differs from the native amino acid sequence $X_1KEFKRIVQRIKDFLRNLVX_6$.

In a second aspect, the invention provides methods for the preparation of such compounds. The methods include the chemical and enzymatic ligation of amino acids monomers or oligomers to assemble the compounds. They also include the expression of nucleic acid sequences encoding the compounds in host cells, using a vector for transfecting the host cells with the nucleic acid sequences. A method for the preparation of a compound according to any one of the previous claims, wherein amino acid monomers, amino acid oligomers, or mono- or oligomers of amino acid analogues or mimetics are assembled by chemical or enzymatic ligation, which is performed in a liquid phase and/or at the interface to a functionalized solid phase.

In a further aspect, the invention relates to the use of the compounds of the invention for preparing pharmaceutical or diagnostic compositions which are suitable for the diagnosis, prevention, and/or treatment of diseases and conditions associated with, or resulting from, the presence of bacterial toxins, especially LPS and LTA. These toxins may affect an organism even when the infective bacteria themselves are no longer present in the organism. Diagnostic compositions comprising the compounds of the present invention may be used in vivo or in vitro. Pharmaceutical compositions comprising the compounds of the invention will typically also contain one or more pharmaceutical carriers and/or excipients, and will be adapted to be useful for a specific route of administration, such as parenteral injection or infusion, locoregional application, such as instillation, irrigation, injection, or infusion; but also for inhalation, oral ingestion, nasal or transmucosal administration, or any other appropriate route. The compositions may further contain drug targeting agents, bioavailability enhancement agents, or active ingredients other than compounds of the invention, and provide for immediate or modified release.

In a further aspect, the invention relates to a nucleic acid sequence encoding a peptide comprising the amino acid sequence $KEFX_2RIVX_3RIKX_4FLRX_5LV$ (SEQ ID NO: 3), wherein $X_2$ is K or E, $X_3$ is Q or E, $X_4$ is D or R, $X_5$ is N or E, wherein $X_2$, $X_3$, $X_4$ and $X_5$ are not at the same time K, Q, D and N, respectively.

Further aspects of the invention will be set forth in the detailed description below and in the appending claims.

DETAILED DESCRIPTION OF THE INVENTION

The compounds of the present invention are peptidic compounds with affinity to lipopolysaccharides (LPS) or lipoteichoic acid (LTA). They comprise the core amino acid sequence $X_1KEFX_2RIVX_3RIKX_4FLRX_5LVX_6$ (SEQ ID NO: 2), wherein $X_1$ represents the N-terminal part of the sequence, $X_2$ is K or E, $X_3$ is Q or E, $X_4$ is D or R, $X_5$ is N or E, $X_6$ represents the C-terminal part; and wherein one or more of the amino acids of the core sequence may be derivatized, wherein the N-terminal part is acetylated and/or the C-terminal part is amidated and/or the amino acid sequence differs from the native amino acid sequence $X_1KEFKRIVQRIKDFLRNLVX_6$.

In this description and the appending claims the terms "wherein the N-terminal part is acetylated" have the following meaning. The N-terminal part is protected by reaction with a carboxylic acid to obtain an amide linked stabilizing or protecting group. It is, for instance, possible to react the peptide with fumic acid to obtain a formyl stabilized peptide; with acetic acid to obtain an acetyl protected peptide. Further the peptide can be reacted with propionic acid and other organic acids having up to 6 carbon atoms and even up to 10 carbon atoms in the carbohydrate part R. In these organic acids the carbohydrate group is R having up to 10 carbon atoms, may be straight, or branched, or cyclic and/or may contain one or more unsaturations. Moreover, the alkyl chain can be substituted with e.g. hydroxyl, halogen, amino, mercapto and sulphuroxide groups. Hence, at the N-terminal part the following group can be present: —C(O)—R'. Alternatively, instead of reaction with a carboxylic acid, the reaction can also be carried out with a sulphonic acid to obtain the corresponding sulfonamide linkage. Hence, at the N-terminal part the group —$SO_2$—R may be present. Alternatively, the said terms also encompass alkylation and dialkylation so that at the N-terminal part a secondary or tertiary amine group —N—$(R)_1$ or N—$(R)_2$ may be present wherein each R has the above meaning.

In yet a further embodiment the "acetylation" encompasses reaction of the peptide with an isocyanate or an isothiocyanate in which case a urea or thiourea is created: R—N—C (O)— or R—N—C(S)— respectively, R being as defined hereinabove.

Finally, the N-terminus can be protected by an acid stable blocking group, which group is conventionally introduced during peptide synthesis, but will now not be removed. Well-known blocking groups are the $F_{moc}$ and Z-group.

As to the meaning of the terms "wherein the C-terminal part is amidated" the following is noted. The term "amidation" means that the —OH naturally present as the C-terminus is replaced by the group —X, wherein X is (i) a —$NY_2$ group, Y, independently being H, or R, wherein R is as defined hereinabove or the two Y-groups together may be a cyclic moiety together with the N-group to which they are attached; (ii) an —OR group wherein R is as defined hereinabove, or (iii) a —R group. The peptide amides are preferred because these have the highest stability.

The peptidic compounds of the present invention have been found to have an optimized stability compared to the native amino acid sequence excluded from claim 1.

Peptidic compounds are peptides, such as oligo- or polypeptides, proteins, or substances derived from peptides. Beyond peptides themselves, peptidic compounds also encompass analogues of peptides, peptide derivatives, modified peptides, and peptide conjugates. Peptidic compounds have in common that they comprise amino acid sequences. More precisely, peptides are defined as amides that are derived from two or more amino acids by combination of the amino group of one acid with the carboxyl group of another (Merriam Webster Medical Dictionary 2001). A peptidic compound, in contrast, may also refer to a peptide structure within a molecule. Typically, peptides are composed of naturally occurring (L-)α-amino acids, in particular alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V).

Analogues or functional equivalents of peptides are peptidic molecules, comprising the same activity and especially the same affinity to microbial and especially to bacterial toxins in kind, but not necessarily in amount, and may, for instance, be modified peptides, peptoids, peptide analogues or peptidomimetics.

Modified peptides are molecules derived from peptides by the introduction of substituents or functional groups which are, generally, not present in naturally occurring amino acids. The term also includes compounds which are obtained by the reaction of peptides with molecules from other chemical categories, whether these molecules are naturally occurring or not. For instance, phosphorylated, sulfonated and biotinylated peptides, glycoproteins, and lipoproteins are frequently found in nature, while peptides modified with polyethylene glycol are examples of chemically modified peptides that have been designed to alter some, but not all of the peptides' properties.

Peptoids, like peptides, are also peptidic compounds. They are also typically amides of two or more amino acids. However, they are frequently not directly derived from naturally occurring amino acids, but rather of various types of chemically synthesized L- and/or D-amino acids.

Peptidomimetics, in their broadest scope, are compounds which are in their functional structure more or less similar to a peptide, but which may also contain non-peptidic bonds in the backbone, or D-amino acids. In general, peptidomimetics serve as substitutes for native peptides in the interaction with receptors and enzymes (Pharmaceutical Biotechnology, Ed. D. J. A. Crommelin and R. D. Sindelar, Harwood Academic Publishers, 1997, p. 138). Pseudopeptides, a class of peptidomimetics, are compounds containing amide bond isosteres instead of amide bonds (ibid., pp. 137-140).

Compounds of the invention also include salts of peptides or functional equivalents, such as pharmaceutically acceptable acid- or base addition salts, and adducts. They also include multimers of peptides or functional equivalents.

The compounds of the invention have affinity to at least one toxin, and especially a bacterial toxin. Particularly, it has been shown that concentrations of peptides of around 1 micromolar show significant (more than 50%) reduction of LPS/LTA activity in vitro. In fact, the term "affinity" as used in this description refers to the activity of the peptides in the assays applied. In these assays, activity of the preferred peptides has been measured to be in the low micromolar to high nanomolar range. More in general, the compounds of the invention have sub-millimolar activity, compounds showing higher affinity, e.g. low micromolar or nanomolar activity, being preferred. In a large number of infectious diseases, bacterial toxins, such as the class of lipopolysaccharides (LPS) in the case of gram-negative bacteria, and lipoteichoic acid in the case of gram-positive bacteria, are involved in the manifestation of the disease. These toxins can induce substantial inflammatory reactions. For instance, in upper airway infections, the inflammation may lead to mucosal damage of the epithelial of the middle ear or the sinuses, resulting in the impairment of the mucociliary clearance system (MCS), which is one of the major defence systems of the upper airways. The compounds of the invention are also particularly suitable for treating intestinal infections. Affinity to the fungal or bacterial toxins is a prerequisite of any neutralization capability, and preferably, the compounds of the invention not only bind to LPS and other toxins, but also have the ability to neutralize, inhibit these toxins or otherwise reduce the effects of said toxins.

The desired type of activity against bacterial toxins is observed when peptidic compounds fulfill the structural requirements as defined in claim 1, according to which the compounds comprise an amino acid sequence $X_1KEFX_2RIVX_3RIKX_4FLRX_5LVX_6$(SEQ ID NO: 2), wherein $X_1$ represents the N-terminal part of the sequence, $X_2$ is K or E, $X_3$ is Q or E, $X_4$ is D or R, $X_5$ is N or E, and $X_6$ represents the C-terminal part. This basic motif is derived from the natural antimicrobial protein CAP18, or the peptide LL-37 which is itself derived from CAP18.

As used herein, the N-terminal part is a group, atom, or sequence representing the N-terminal moiety or domain of the compound, i.e. the structure that is attached to the terminal α-amino group of the core sequence which is not involved in an amide bond within the sequence. The N-terminal part may simply be a hydrogen atom in the case of a free α-amino group; or it may consist of a chemical group attached to the terminal α-amino nitrogen atom, such as an acyl group. It may also represent a larger group, such as a sequence of two or more amino acids, or a chemical structure which is not composed of or not solely composed of amino acids. The C-terminal part is defined in an analogue fashion.

Preferably, the compounds of the present invention comprise a total of more than the 18 amino acids defining the core motif. In one embodiment, the N-terminal part comprises a sequence of two or more amino acids. Among the amino acids which are suitable members of this sequence are I and G, and a preferred N-terminal part is IG.

In another embodiment, the C-terminal part also comprises an amino acid sequence. The sequence may comprise 1, 2, 3, 4, or more than 4 amino acids. In one embodiment, the C-terminal part comprises 4 amino acids. The C-terminal end of said C-terminal part of 4 amino acids may be an E, as in the equivalent position within peptide LL-37. However, this C-terminal end may also be defined by an R. The amino acid which is positioned next to the C-terminal amino acid may be T as in LL-37, or it may be L. P and R are two other preferred members of the 4 amino acid sequence of the C-terminal part, in either of the two remaining positions. Most preferably, the C-terminal part is selected from the sequences PRTE and RPLR.

In a further embodiment, the N-terminal part and the C-terminal part are selected from the preferences described above to yield a peptidic structure with a total number of 24 amino acids. Among the presently most preferred compounds are the peptides IGKEFKRIVQRIKDFLRNLVPRTE (SEQ ID NO: 4) and IGKEFKRIVERIKRFLRELVRPLR (SEQ ID NO: 5), either as peptides themselves, or as modified or derivatized peptides.

Among the preferred modifications are amidated and/or acetylated peptides according to the above definitions. One of the positions in which amidation seems particularly advantageous is the C-terminus of the peptide. Acetylation, on the other hand, is preferably performed at the N-terminal amino acid. In one of the presently preferred embodiments, the peptides IGKEFKRIVQRIKDFLRNLVPRTE (SEQ ID NO: 4) and IGKEFKRIVERIKRFLRELVRPLR (SEQ ID NO: 5) are both N-terminally acetylated and C-terminally amidated. Preliminary testing suggested that these modifications possess an increased stability in the presence of exo-peptidases.

The compounds can generally be prepared by the methods that are known for the preparation of peptides and similar substances. Smaller compounds containing only a few amino acids or similar units, and preferably not more than 30-50 units, can be prepared by chemical or enzymatic ligation techniques, either using the classical approach in which the reactions take place in solution or suspension, or by employing the more modern solid phase approach, in which the peptide is assembled while being anchored to a solid surface, such as a polymeric bead. Larger compounds are typically synthesized by automatic solid phase peptide synthesizers.

Alternatively, the compounds can be prepared by known genetic engineering techniques. This approach is especially valid if the compound is indeed a peptide or a slightly modified peptide. For instance, a DNA sequence which encodes the compound can be associated or combined with an expression vector capable of transfecting cells. In another step of the method, host cells or target cells are transfected with said DNA by contacting the cells with the vector and the vector-associated DNA under conditions which allow transfection. In a further step, the host or target cells are cultured under conditions which allow the expression of the compound. Subsequently, the compound can be isolated. If the compound itself cannot be encoded or expressed but is very similar to a peptide that can be encoded or expressed, the method can be applied to prepare the peptide to which the compound is similar, followed by one or more steps wherein the peptide is modified by chemical or enzymatic techniques to prepare the compound.

Various types of vectors are used for this purpose, such as viral vectors, lipoplexes, polyplexes, microspheres, nanospheres, dendrimers, naked DNA, peptide delivery systems, lipids, especially cationic lipids, or liposomes made thereof, polymeric vectors, especially those made of polycationic polymers. Among the preferred viral vectors are retroviruses, adenoviruses, adeno-associated viruses, herpes simplex viruses, and virosomes. Preferred non-viral vectors include chitosan, SPLP, polymeric systems based on PLGA, polyethyleneimines, polylysines, polyphosphoamidates, poly(meth) acrylates, polyphosphazenes; DOPE, DOTAP, and DOTMA.

Some more comprehensive summaries of methods which can be applied in the preparation of the compounds of the invention are described in: W. F. Anderson, Nature 392 Supp., 30 Apr. 1998, p. 25-30; Pharmaceutical Biotechnology, Ed. D. J. A. Crommelin and R. D. Sindelar, Harwood Academic Publishers, 1997, p. 53-70, 167-180, 123-152, 8-20; Protein Synthesis: Methods and Protocols, Ed. R. Martin, Humana Press, 1998, p. 1-442; Solid-Phase Peptide Synthesis, Ed. G. B. Fields, Academic Press, 1997, p. 1-780; Amino Acid and Peptide Synthesis, Oxford University Press, 1997, p. 1-89.

Salts of peptides or functional equivalents are prepared by known methods, which typically involve the mixing of the peptide or peptoid with either a pharmaceutically acceptable acid to form an acid addition salt, or with a pharmaceutically acceptable base to form a base addition salt. Whether an acid or a base is pharmaceutically acceptable can be easily decided by a person skilled in the art after taking the specific intended use of the compound into consideration. For instance, not all acids and bases that are acceptable for in vitro diagnostic compositions can be used for therapeutic compositions. Depending on the intended use, pharmaceutically acceptable acids include organic and inorganic acids such as formic acid, acetic acid, propionic acid, lactic acid, glycolic acid, oxalic acid, pyruvic acid, succinic acid, maleic acid, malonic acid, cinnamic acid, sulfuric acid, hydrochloric acid, hydrobromic acid, nitric acid, perchloric acid, phosphoric acid, and thiocyanic acid, which form ammonium salts with free amino groups of peptides and functional equivalents. Pharmaceutically acceptable bases, which form carboxylate salts with free carboxylic groups of peptides and functional equivalents, include ethylamine, methylamine, dimethylamine, triethylamine, isopropylamine, diisopropylamine, and other mono-, di- and trialkylamines, as well as arylamines. Moreover, also pharmaceutically acceptable solvates, complexes or adducts, such as hydrates or ethurates are encompassed.

Some of the preferred modifications of the peptides according to the invention may be easily introduced during or at the end of the synthesis. For instance, when the peptide is synthesized using a solid-phase technique, N-terminal acetylation can be performed at the end by reacting the amino acid sequence, which is still bound to the resin, with acetic acid instead of with another amino acid.

C-terminal amidation, on the other hand, can be performed by using a special kind of resin in solid-phase peptide synthesis, such as the commercially available Tentagel S AM (ex Rapp, Tübbingen, Germany). These resins comprise a chemical "handle" from which amidated peptides are released during the cleavage. These and further methods of modifying peptides are known to any person skilled in the art.

A further aspect of the invention relates to the use of the peptidic compounds. The compounds have an affinity to microbial toxins and especially to bacterial toxins, such as lipopolysaccharide (LPS) and lipoteichoic acid (LTA). Therefore, the compounds can be used advantageously for therapeutic and diagnostic purposes in conditions and diseases in which the presence of these toxins is involved. The binding ability will typically lead to neutralization of the toxins, by virtue of which the compounds may be considered antagonists or partial antagonsists. Furthermore, they may be used as targeting agents or ligands for other compounds which are capable of neutralizing the toxins, and which may be specifically targeted to these toxins through covalent or non-covalent ligation with the compounds, or through being covalently or non-covalently bonded to the surface of a drug carrier such as a liposome, a nano- or microparticle, a nano- or microcapsule, a lipid complex, or a micelle.

In diagnosis, the compounds may be used for the detection of, or the quantification of the amount of, bacterial toxins present in physiological fluids, such as the blood, plasma, serum, the mucus lining a mucosal epithelium, such as of the respiratory tract, or in fluids whose presence results from a pathological condition, such as the fluid found in the middle ear in otitis media with effusion (OME). For this use, the compounds may be incorporated into diagnostic kits to be used in vitro, or into diagnostic compositions which may be administered to a patient. For this use, an option is to conjugate a compound of the invention with a chelator, which is subsequently complexed with an isotopic label that is detectable by an appropriate monitoring system.

In a preferred use, the compounds are administered as active drug substances to prevent or treat diseases and conditions related to fungal and bacterial infections and the presence of fungal and bacterial toxins in the body. As mentioned before, there are certain disadvantages and limitations of antibiotic therapy in acute or chronic infections, such as the induction of tolerance and the selection of tolerant bacterial variants, the depression of the patient's natural defence systems, the impairment of the bacterial flora naturally populating the mucosae, the release of large amounts of bacterial toxins as the germs are killed etc. Furthermore, there may be conditions and diseases in which the presence of toxins and especially bacterial toxins, and not the presence of the microorganisms per se, is the major cause, such as in OME, wherein the local retention of toxins in the middle ear may significantly contribute to the manifestation of the disease even in the absence of symptoms of an acute infection.

In all these cases, it may be advisable to treat the disease not with antibiotic drugs, but with substances which are capable of neutralizing the bacterial toxins. For this aim, the compounds of the invention are particularly advantageous because they show a high binding and neutralization activity against the most relevant microbial toxins, such as lipopolysaccharide (LPS) in the case of gram-negative bacteria, and lipoteichoic acid (LTA) in the case of gram-positive bacteria. In infections of the upper airways, for the treatment of which the compounds of the invention are particularly preferred, these bacterial products can induce an inflammation reaction in the middle ear or in the sinuses, and can induce mucosal damage of the upper airway epithelia. Neutralizing the toxins involved may allow the mucosal damage including the impairment of the mucociliary clearance system (MCS) to be prevented, controlled, or reduced, and will thus strengthen the natural defence systems. In those cases including OME, in which bacterial toxins may represent the major problem even in the absence of significant numbers of living bacterial cells, a therapy relying on the administration of a compound of the invention, for instance directly to the middle ear, may represent the primary therapeutic approach. But also in other airway infections, such as acute or chronic sinusitis, or acute or chronic otitis, the compounds may be highly useful for the restoration of the normal mucosal functions and their natural defense systems.

More generally speaking, the compounds of the invention are useful agents in the prevention and therapy of conditions arising from infective bacteria including *Streptococcus pneumoniae, Haemophilus influenzae, Moraxella catarrhalis*, group A β-hemolytic streptococci, *Staphylococcus aureus*, gram-negative enteric bacilli, *Streptocossus pyogenes, Escherichia coli*, gram-negative bacilli, *Pseudomonas* sp.

A particular advantage of the compounds of the invention over the native proteins and peptides from which they are derived, such as CAP18 and LL-37, is their low degree of undesirable inflammatory activity. This activity is related to the various cellular processes, including proliferation, differentiation and expression of genes encoding pro-inflammatory mediators like cytokines. Cytokines are direct mediators of inflammation and influence the progress and direction of many immunological reactions. Perturbation of the balance in cytokine production is widely recognized as a critical factor in several disease states. In a condition such as otitis media with effusion or sinusitis, this balance is already disturbed. T cell proliferation is also not favorable in this situation, because this will further stimulate the immune response that is already out of control.

Thus, the compounds can be advantageously used in pharmaceutical compositions. According to the invention, such pharmaceutical compositions are provided as well as the compounds themselves. As used herein, the term "pharmaceutical composition" refers to therapeutic and diagnostic compositions, as well as to medicaments and diagnostics containing such compositions. Therapeutic compositions and medicaments are used for the prevention or treatment of diseases and other conditions of mammals whose improvement is desirable. Diagnostics and diagnostic compositions are used for the diagnosis of such diseases in vivo and in vitro.

Typically, such a composition comprises at least one compound of the invention as active ingredient and at least one pharmaceutically acceptable carrier or excipient. Furthermore, the composition is processed and shaped in such a way that it can be administered to a human being, or to an animal. As used herein, a carrier or excipient is any pharmaceutically acceptable substance or mixture of substances having no substantial pharmacological activity, which can be used as a vehicle or as an auxiliary substance to formulate a compound into dosage form which is stable and suitable to administer. Examples of pharmaceutically acceptable excipients are known to the skilled man and can be found in the monographs of the major pharmacopoeias.

In one embodiment, the composition is formulated and processed for parenteral injection, instillation or irrigation, preferably for intravascular injection, such as intravenous or intra-arterial, but also for intramuscular, subcutaneous, intralesional, intraperitoneal, locoregional or other routes of parenteral administration. In another preferred embodiment, the composition is administered directly to the affected mucosa of the upper airway, such as the middle ear. The same principles that govern the formulation of other drugs for these administration routes will also teach those skilled in the arts on how to prepare such compositions. For instance, one of the requirements of parenteral dosage forms is their sterility.

Other requirements are described in all major pharmacopoeias, such as in USP 24, in the monograph "General Requirements for Tests and Assays. 1. Injections", p. 1775-1777. To increase the stability of a parenteral formulation, it may be necessary to provide a dried dosage form which must be reconstituted before it can be administered. An example of such a dosage form is a freeze-dried or lyophilized formulation. Suitably, the compositions of the invention may also contain a mucolytic solvent.

It may be desirable to administer a compound of the invention as a parenteral controlled release dosage form to avoid frequent injections and to improve the effectiveness and convenience of the therapy. Various methods of preparing such depot formulations are known. Prolonged release may be provided by solid implants, nanoparticles, nanocapsules, microparticles, microcapsules, emulsions, suspensions, oily solutions, liposomes, or similar structures.

In the case of compositions which are to be administered locally to an affected mucosa, it may be useful to provide a formulation having properties which provide for an extended time of local retention at the site of administration to increase the effectiveness of the medication. To achieve this goal, mucoadhesive excipients may be incorporated into the formulation. Such functional excipients are known to the person skilled in the art; they include polymers such as polyacrylic acids and derivatives thereof, polymethacrylic acids and their derivatives, cellulose ethers including hydroxypropyl methylcellulose, carboxymethylcellulose, starches, chitosan etc. Suitably or alternatively, the compositions of the invention may also contain a mucolytic solvent. Particularly, mucolytic solvents are used to affect the permeability of the peptidic compound of the invention into the mucus, e.g. in the respiratory tract. Suitable solvents may comprise known mucoregulatory or mucolytic agents such as N-acetylcysteine, S-carboxymethyl cysteine, bromhexine, ambroxyl, DNAse, erdosteine, saline solution and nesosteine. Preferably, bromhexine is used.

Further excipients that are particularly useful for the preparation of parenteral formulations in their broadest definition are solvents, cosolvents and liquid or semisolid carriers, such as sterile water, ethanol, glycerol, propylene glycol, polyethylene glycol, butanediol, fatty oils, short- and medium chain triglycerides, lecithin, polyoxyethylene castor oil derivatives; substances to adjust the osmolality and pH, such as sugars, especially glucose, sugar alcohols, especially mannitol, sodium chloride, sodium carbonate, citric acid, acetate, phosphate, phosphoric acid, hydrochloric acid, sodium hydroxide etc.; stabilizers, antioxidants, and preservatives, such as ascorbic acid, sodium sulfite or -hydrogen sulfite, EDTA, benzyl alcohol etc.; other excipients and lyophilization aids, such as albumin, dextran etc.

Similarly, it may be advantageous to administer a compound of the invention in a transmucosal dosage form. This route of administration is non-invasive and patient-friendly; at the same time it generally leads to an improved bioavailability of the compound of the invention as compared to oral administration, especially if the compound is not stable in the fluids of the digestive system, or if it is too large to be absorbed from the gut effectively. Transmucosal administration is possible, for instance, via nasal, buccal, sublingual, gingival, or vaginal dosage forms. These dosage forms can be prepared by known techniques; they can be formulated to represent nasal drops or sprays, inserts, films, patches, gels, ointments, or tablets. Preferably, the excipients used for a transmucosal dosage form also include one or more substances providing for mucoadhesion, thus prolonging the contact time of the dosage form with the site of absorption and thereby potentially increasing the extent of absorption.

Alternatively, the pharmaceutical compositions may be designed for oral administration and processed accordingly. Appropriate oral dosage forms include tablets, hard capsules, soft capsules, powders, granules, orally disintegrating dosage forms, syrups, drops, suspensions, effervescent tablets, chewable tablets, oral films, lyophilized dosage forms, sustained release dosage forms, controlled release dosage forms. In one of the preferred embodiments, the oral dosage form is an enterically coated solid dosage form to provide protection of the compound from the acidic and proteolytic environment of the stomach.

The compositions can also be formulated for intestinal administration.

In a further embodiment, the compounds are administered via the pulmonary route, using a metered dose inhaler, a nebulizer, an aerosol spray, or a dry powder inhaler. Appropriate formulations can be prepared by known methods and techniques. Transdermal, rectal, or ocular administration may also be feasible in some cases.

It can be advantageous to use advanced drug delivery or targeting methods to deliver a compound of the invention more effectively. For instance, if a non-parenteral route of administration is chosen, an appropriate dosage form may contain a bioavailability enhancing agent, which may be any substance or mixture of substances which increases the availability of the compound. This may be achieved, for instance, by the protection of the compound from degradation, such as by an enzyme inhibitor or an antioxidant. More preferably, the enhancing agent increases the bioavailability of the compound by increasing the permeability of the absorption barrier, which is typically a mucosa. Permeation enhancers can act via various mechanisms; some increase the fluidity of mucosal membranes, while others open or widen the gap junctions between mucosal cells. Still others reduce the viscosity of the mucus covering the mucosal cell layer. Among the preferred bioavailability enhancers are amphiphilic substances such as cholic acid derivatives, phospholipids, ethanol, fatty acids, oleic acid, fatty acid derivatives, EDTA, carbomers, polycarbophil, and chitosan.

The following examples are intended to further illustrate the invention, but not to limit its scope to the embodiments presented herein.

INCORPORATION OF SEQUENCE LISTING

Incorporated herein by reference in its entirety is the Sequence Listing for the application. The Sequence Listing is disclosed on a computer-readable ASCII text file titled, "sequence_listing.txt", created on Nov. 13, 2008. The sequence_listing.txt file is 4 kb in size.

Example 1

Preparation of Compounds

The following peptidic compounds, each of them comprising 24 amino acids, the compounds herein coded as P60, P60.4, P60.Ac, and P60.4Ac were prepared by solid phase strategies on an automated multiple peptide synthesizer (SyroII, MultiSyntech, Witten, Germany). For P60 and P60.4, Tentagel S AC (Rapp, Tübingen, Germany), a graft polymer of polyethyleneglycol and polystyrene was used as a resin (loading 0.2 meq, particle size 90 µm). For P60Ac and P60.4Ac, Tentagel S AM was used, which yields a C-terminally amidated peptide. Repetitive couplings were performed by adding a six fold molar excess (based on the resin loading) of a 0.60 M solution of the appropriate Fmoc amino acid in NMP, a six fold molar excess of 0.67 M PyBOP in NMP and a twelve fold molar excess of NMM in NMP 2/1 (v/v) to the reaction vessel. Side chain protection was as follows: tBu for D, E, S, T; Boc for K; Trt for N, Q and Pmc for R. Fmoc-deprotection was performed by adding 3 times piperidine/NMP 1/4 (v/v) to each reaction vessel. Coupling- and deprotection times were 45 min and 3 times 3 min, respectively. Washings after couplings and Fmoc-deprotections were performed 6 times with NMP. For P60.Ac and P60.4Ac, the N-terminal acetylation was performed with acetic acid while the peptide was still bound to the resin. After synthesis the peptidyl resins were washed extensively with NMP, dichloromethane, dichloromethane/ether 1/1 (v/v) and ether respectively, and air dried. Peptidyl resins were then cleaved and side chain deprotected in TFA/water 95/5 (v/v) for 2.5 h (1.5 ml per 10 µmol of peptide), the resin was removed by filtration and the peptide was precipitated from the TFA solution with ether/pentane 1/1 (v/v) (10 ml per 10 µmol of peptide). The solution was cooled for 1 h at −20° C. and the precipitated peptide was isolated by centrifugation (−20° C., 2,500 g, 10 min). After triturating and vortexing of the pellet with 10 ml ether/pentane 1/1 (v/v) and isolation by the same procedure, the peptides were air dried at room temperature for 1 h. Peptides were dissolved in 2 ml water or 2 ml 10 vol % acetic acid, the solution was frozen in liquid nitrogen for about 5 min and subsequently lyophilized while being centrifuged (1,300 rpm, 8-16 h). The analysis of the peptides was performed with RP-HPLC and Maldi-Tof mass spectrometry.

The amino acid sequences of the compounds are:

P60 IGKEFKRIVQRIKDFLRNLVPRTE (SEQ ID NO: 4)

P60.Ac* IGKEFKRIVQRIKDFLRNLVPRTE (SEQ ID NO: 4)

P60.4 IGKEFKRIVERIKRFLRELVRPLR (SEQ ID NO: 5)

P60.4Ac* IGKEFKRIVERIKRFLRELVRPLR (SEQ ID NO: 5)

*The suffix Ac means that the peptide is N-terminally acetylated and C-terminally amidated.

Example 2

Neutralization of Toxins

Compounds prepared according to example 1 were tested for their capability to neutralize the bacterial toxin LPS with a *limulus* amoebocyte lysate (LAL) assay and with a whole blood (WB) assay. LTA neutralization was also measured with a whole blood assay. Peptide LL-37 was used as a positive control. The peptide concentration whereby 50% LPS is neutralized (50% inhibition) was used as a measure of the peptide's activity. These concentration values were as in table 1. The differences between the compounds within each assay were not statistically significant. In summary, the tested compounds of the invention showed approximately the same degree of anti-toxin activity as the native antimicrobial peptide LL-37.

TABLE 1

50%-LTA inhibition values (±SD) in µg/ml and the 50%-LPS inhibition values (±SD) in µg/ml for LL-37, P60, P60.4 and P60.Ac. LTA-inhibition was tested in the whole blood (WB) assay. LPS-inhibition was tested in LAL-assay as well as in the whole blood assay. The synthetic peptides induced an LTA-neutralization which was not significantly different from LL-37. LPS-neutralization induced by the synthetic peptides was also not significantly different from LL-37.

| Peptide | 50%-LTA inh. (µg/ml), n = 3 | 50%-LPS inhibition (µg/ml) | | |
|---|---|---|---|---|
| | | LAL-assay | WB-assay | Average |
| LL-37 | 1.6 ± 0.5 | 1.3 ± 0.2 (n = 5) | 1.2 ± 0.2 (n = 3) | 1.3 ± 0.2 (n = 8) |
| P60 | 2.1 ± 0.7 | 1.5 ± 0.5 (n = 5) | 1.4 ± 0.1 (n = 4) | 1.5 ± 0.3 (n = 9) |
| P60.4 | 2.0 ± 1.3 | 1.7 ± 0.6 (n = 5) | 2.1 ± 0.6 (n = 2) | 1.8 ± 0.6 (n = 7) |
| P60.Ac | 2.1 ± 0.1 | 1.8 ± 0.8 (n = 5) | 2.4 ± 0.5 (n = 2) | 2.0 ± 0.8 (n = 7)) | n = number of experiments.

Example 3

Immunologic Cell Activation by Compounds

The compounds prepared according to example 1 were tested for their therapeutically undesirable immunogenic activity by using Elispot, T-cell proliferation, ERK-activation, and neutrophil chemotaxis assays. The Elispot assay is applicable to determine effects of drugs, chemicals or other compounds on cytokine secretion in vitro, thereby providing data on their putative modulatory effects on immune function in vivo. The results of the assay are given as fraction of positive responses to IFN-gamma. ERK-(extracellular signal-related kinases)-1/2 is part of the MAP-kinase signaling pathway, that has been shown to be involved in various cellular processes, including proliferation, differentiation and expression of genes encoding pro-inflammatory mediators like cytokines. Cytokines are direct mediators of inflammation and influence the progress and direction of many immunological reactions. Perturbation of the balance in cytokine production is widely recognized as a critical factor in several disease states. This balance is already disturbed in the case of conditions such as otitis media with effusion and sinusitis. T cell proliferation is also not favorable in this situation, because this will also stimulate the immune response that is already out of control. It is therefore desirable that the compounds of the invention do not stimulate cytokine production, T cell proliferation, ERK-activation or chemotaxis of neutrophils.

For T cell proliferation, 150,000 peripheral blood mononuclear cells (PBMC) were cultured in the absence or presence of 10 µg/ml of the compounds for 5 days in 96 well round bottom plates (Costar Inc. Cambridge, Mass.) in a final volume of 150 µl IMDM complete. As a positive control, PBMC were cultured in the presence of 25 U/ml recombinant IL-2. During the final 20 hours of culture, PBMC were pulsed with [3H] thymidine (0.5 microCi/well), after which $^3$H-incorporation was measured by liquid scintillation counting. For detection of the T cell cytokines IFN and IL-10 by Elispot analysis, $1.5 \times 10^6$ PBMC were cultured in 0.5 ml IMDM complete in the absence or presence of various concentrations of synthetic peptide. As a positive control PBMC were stimulated by 10 µg/ml poke weed mitogen (PWM). After 48 hours of culture, PBMC were harvested by gently rinsing the wells with warm IMDM to collect non-adherent cells, which were washed in a large volume of IMDM. PBMC were subsequently plated on antibody-precoated ELISA plates and cultured for 5 hours in IMDM supplemented with 2% pooled human AB serum at 37° C. 5% $CO_2$, after which the plates were developed according to the manufacturer's protocol (U-CyTech, Utrecht, The Netherlands). Spots were counted on an Olympus microscope and analyzed with Olympus Micro Image 4.0 software (Paes Nederland, Zoeterwoude, The Netherlands). The final results are expressed as fraction of positive stimulation indices (positiv: >2).

ERK-1/2 activation was tested with cells from the mucoepidermoid lung tumor cell line NCI-H292 (ATCC, Rockville, Md.), which were cultured in 24- or 6-well tissue culture plates in RPMI1640 medium (Gibco, Grand Island, N.Y.) supplemented with 2 mM L-glutamine (Bio Wittaker, Walkersville, Md.), 200 U/ml penicillin (Bio Wittaker), 200 µg/ml streptomycin (Bio Wittaker) and 10% (v/v) heat-inactivated fetal calf serum (Gibco). After reaching near-confluence, cells were cultured overnight in serum-free medium. Cells were subsequently stimulated for 15 minutes with indicated stimuli. Cellular lysates were prepared using lysis buffer (0.5% [v/v] Triton X-100, 0.1M Tris-HCl pH 7.4, 100 mM NaCl, 1 mM $MgCl_2$, 1 mM $NaSVO_4$, mini complete protease inhibitor cocktail [Boeringer Mannheim, Roche, Basel, Switzerland]). Samples were subjected to SDS-PAGE on a 10% glycine-based gel, and resolved proteins were transferred to a polyvinylidene difluoride (PVDF) membrane. Non-specific binding sites were blocked by PBS/0.05% Tween-20/1% casein. The blots were incubated with rabbit polyclonal antibodies against phosphorylated ERK-1/2 (New England Biolabs, Beverly, Mass.), and secondary horseradish peroxidase conjugated anti-rabbit IgG antibodies. The enhanced chemoluminescent (ECL) Western blotting detection system (Amersham Pharmacia Biotech, Upsala, Sweden) was used to reveal immunoreactivity.

Neutrophils chemotaxis was measured with neutrophils isolated from peripheral blood using Percoll density centrifugation (density: 1.082 g/ml). The cells were resuspended at a concentration of $2.5\times10^6$ cells/ml in chemotaxis medium (20 mM N-2-hydroxyethylpiperazine-N'-2-ethanesulfonic acid (HEPES buffer) HEPES, 132 mM NaCl, 6 mM KCl, 1.2 mM $KH_2PO_4$, 1 mM $MgSO_4$, 5.5 mM glucose, 0.1 mM $CaCl_2$ and 0.5% (wt/vol) human serum albumin [Central Laboratory of the Netherlands Red Cross Blood Transfusion Service (CLB), Amsterdam, The Netherlands] diluted 1:1 with serum-free RPMI. The chemotactic activity of the compounds was assessed using a modified Boyden Camber technique. Briefly, 26 µl stimuli diluted in HEPES buffer was added to the wells of the lower compartment, and 50 µl of neutrophil suspension ($2.5\times10^6$ cells/ml) was added to the upper compartment. The compartments were separated by two filters: a lower filter with a pore size of 0.45 µm (Millipore Products, Bedford, Mass.) and an upper filter with a pore size of 8 µm (Sartorius Filter, San Francisco, Calif.). After incubation for 90 minutes at 37° C., the upper filters were removed, fixed in ethanol-butanol (80:20, vol/vol), and stained with Weigert solution. To determine neutrophil chemotactic activity, neutrophils were counted in six random high-power fields (×400), and the percentage neutrophils on the membrane as compared to the positive control (10-8 M N-formylmethionyl-leucyl-phenylalanine (FMLP, Sigma) was calculated.

The results are given in table 2. In summary, the tested compounds of the invention, and in particular P60.4, induced a very low immune response, lower than the natural peptide LL-37. They showed a low ERK-activation and virtually no neutrophil chemotaxis.

TABLE 2

Immunogenicity of compounds

| Compound | γ-IFN Elispot | T cell proliferation | ERK-activation | Chemotaxis (%) |
|---|---|---|---|---|
| P60 | 1/8 | 0/8 | – | 76 ± 39 |
| P60.Ac | 3/8 | 0/8 | ± | 61 ± 36 |
| P60.4 | 3/8 | 0/8 | ± | 0 ± 0 |
| P60.4Ac | nd | 0/8 | ± | 24* |
| LL-37 (control) | 4/8 | 4/8 | + | 84 ± 17 |

*only one measurement

Example 4

In-Vivo Tolerability

Compound P60.4Ac was prepared according to example 1 and tested for its tolerability in vivo. More specifically, its potential for causing skin and eye irritation was evaluated in rabbits, whereas its ototoxicity was studied in a guinea pig model. Furthermore, its systemic toxicity was assessed after intravenous administration.

For the skin and eye irritation tests, three rabbits were exposed to 0.5 ml phosphate buffered peptide solution (2 mg/ml), applied onto clipped skin for 4 hours using a semi-occlusive dressing. Observations were made 1, 24, 48, and 72 hours after exposure. Single samples of 0.1 ml of phosphate buffered (pH7.5) peptide solution (2 mg/ml) were instilled into one eye of each of three rabbits to perform an acute eye irritation/corrosion study. Observations were made 1, 24, 48, and 72 hours after instillation.

In result, no skin irritation was detectable. Ophthalmic instillation of the peptide solution resulted in redness of the conjunctivae which resolved completely within 24 hours after instillation.

The systemic toxicity of P60.4Ac was assessed in a single and repeated dose toxicity study in rats. The peptide was administered daily intravenously in escalating doses. In this phase, the Maximum Tolerated Dose (MTD) was established. Repeated dose toxicity was also studied in the MTD phase. In the dose escalation phase, 9 rats were divided in three groups and received 0.4, 2 or 8 mg/kg/day for two days. Clinical signs were recorded twice daily on days of dosing and one day after dosing, body weights were recorded prior to the first dose and one day after dosing. In the MTD phase, 5 female and 5 male rats received 8 mg/kg/day for 5 following days. Clinical signs were recorded twice daily on days of dosing, body weight on day 1 and 6. Clinical laboratory investigations were performed prior to necropsy. Macroscopy was performed at termination of the MTD phase.

In result, no mortality occurred in the systemic dose escalation study. Furthermore, no clear deviations were noted in clinical signs and body weight. During the MTD phase also no mortality occurred and no clear peptide related findings were noted in clinical signs, body weight, hematology and clinical biochemistry parameters and at macroscopic examination.

For evaluating the ototoxicity, nine healthy male albino guinea pigs (500-1200 g), free of external ear pathology, were used. Animals were anesthetized with intraperitoneal injections of ketamine 40 mg/kg and rompun 10 mg/kg. After control auditory testing was performed, the auditory bullae were surgically opened to apply a small piece of spongostan to the round window membrane (RWM) and various solutions (approximately 10 μL) were added on the spongostan. The skin was sutured closed and follow-up auditory testing was performed.

The guinea pigs were divided into three groups, each consisting of two animals to be treated and one control animal. Test and control formulations were administered onto the RWM of the right ears, while the left ears remained untreated. In group 1, two guinea pigs received cisplatin (0.66 mg/ml in PBS) and one animal received PBS as a control. Cisplatin, whose ototoxicity is known, served as a positive control for the test. Group 2 received the peptide (2 mg/ml) in phosphate buffer (pH7.5) and group 3 received the peptide (2 mg/ml) in formulation solution comprising 7% macrogol 10,000 in isotonic sodium chloride solution preserved with 0.02% benzalkonium chloride and 0.1% Na$_2$EDTA, buffered at pH 5.5 with phosphate.

Auditory brainstem response (ABR) was performed prior to drug administration and directly after surgery and 3, 7, 14 and 22 days later, using a computer-based signal averaging system (Tucker-Davis Technology, Alucha, Fla., USA). Guinea pigs were anesthetized and an insert earphone was placed into the external ear canal. Subcutaneous electrodes were placed over the vertex (active) and over the ipsilateral bulla (reference). Ground electrodes were placed over the neck muscles. ABRs were recorded in an electrically shielded, double-walled, radio-frequency-shielded sound chambre in response to 10 ms tone bursts at 1 kHz. Stimulus intensities were measured and expressed as dB. ABR treshold was defined as the lowest intensity capable of eliciting a replicable, visually detectable response. The post-treatment ABR tresholds were compared to pre-treatment ABR tresholds.

In result, round window application of PBS in group 1 resulted in a threshold change of −9 dB at 22 days after surgery, whereas cisplatin induced threshold changes of −49 dB and −64 dB, respectively (see table 3). In the second group, application of phosphate buffer did not produce a threshold change (see table 4). Phosphate buffer with 2 mg/ml peptide induced a threshold change of −7 dB 22 days after surgery. In one animal, the bulla could not be opened and this animal was excluded from the study. In the last group, the administration of the peptide formulated in the formulation solution produced very small threshold changes of 2 and 1 dB, respectively (see table 5).

TABLE 3

Ototoxicity of cisplatin (positive control)

| | Group 1 | | | | | |
|---|---|---|---|---|---|---|
| | PBS only | | Cisplatin in PBS | | Cisplatin in PBS | |
| | treshold (dB) | Δ pre-surgery | treshold (dB) | Δ pre-surgery | treshold (dB) | Δ pre-surgery |
| presurgery | 86 | | 58 | | 82 | |
| postsurgery | 72 | −14 | 56 | −2 | 81 | −1 |
| 3 days | 67 | −19 | 26 | −32 | 44 | −38 |
| 7 days | 76 | −10 | 26 | −32 | 37 | −45 |
| 14 days | 78 | −8 | 28 | −30 | 23 | −59 |
| 22 days | 77 | −9 | 9 | −49 | 18 | −64 |

TABLE 4

Lack of ototoxicity of P60.4Ac (2 mg/ml) in phosphate buffer

| | Group 2 | | | |
|---|---|---|---|---|
| | PBS only | | P60.4Ac in PBS | |
| | treshold (dB) | Δ presurgery | treshold (dB) | Δ presurgery |
| presurgery | 77 | | 72 | |
| postsurgery | 78 | 1 | 70 | −2 |
| 3 days | 74 | −3 | 70 | −2 |
| 7 days | 74 | −3 | 72 | 0 |
| 14 days | 77 | 0 | 60 | −12 |
| 22 days | 77 | 0 | 65 | −7 |

The invention claimed is:

1. A peptidic compound with affinity to bacterial and fungal toxins, and especially to lipopolysaccharide (LPS) or lipoteichoic acid (LTA) comprising the amino acid sequence IGKEFKRIVERIKRFLRELVRPLR (SEQ ID NO: 5), wherein one or more of the amino acids of the sequence are optionally derivatized, wherein the N-terminal part is acetylated and/or the C-terminal part is amidated.

2. The compound according to claim 1, wherein the N-terminus is acetylated.

3. The compound according to claim 1, wherein the C-terminus is amidated.

4. The compound according to claim 1, wherein the N-terminus is acetylated and the C-terminus is amidated.

5. A pharmaceutical composition, comprising the compound according to claim 1, and one or more pharmaceutically acceptable carriers or excipients.

6. The pharmaceutical composition according to claim 5, being formulated, processed, and adapted for parenteral administration, preferably for intravascular, intramuscular, subcutaneous, or intralesional injection.

7. The pharmaceutical composition according to claim 5, being formulated, processed, and adapted for the local administration to the mucosa of an affected region or tissue, such as in form of an irrigation liquid, ear drops, nose drops, an aerosol, a powder aerosol, a liquid for nebulization, a gel, a suspension, or a mucoadhesive dosage form.

8. The pharmaceutical composition according to claim 5, further comprising a drug targeting agent, a bioavailability enhancing agent, and/or a controlled delivery agent.

9. A method of treating a fungal or bacterial infection induced by lipopolysaccharide (LPS) or lipoteichoic acid (LTA) in a human in need thereof, said method comprising administering to a mammal an effective amount of a peptidic compound with affinity to bacterial and fungal toxins, and especially to lipopolysaccharide (LPS) or lipoteichoic acid (LTA), which comprises the amino acid sequence set forth in SEQ ID NO: 5, wherein one or more of the amino acids of the sequence are optionally derivatized; wherein the N-terminal part is acetylated and/or the C-terminal part is amidated.

10. The method according to claim 9, wherein said infection is a middle ear infection, upper respiratory infection, acute sinusitis, chronic sinusitis, acute otitis, chronic otitis, and/or otitis media.

11. A method of treating an infection in a human in need thereof, said method comprising administering to a mammal an effective amount of a peptidic compound with affinity to bacterial and fungal toxins, and especially to lipopolysaccharide (LPS) or lipoteichoic acid (LTA), which comprises the amino acid sequence set forth in SEQ ID NO: 5, wherein one or more of the amino acids of the sequence are optionally derivatized, wherein the N-terminal part is acetylated and/or the C-terminal part is amidated; wherein said infection is selected from the group consisting of a middle ear infection, upper respiratory infection, acute sinusitis, chronic sinusitis, acute otitis, chronic otitis, and/or otitis media with effusion.

* * * * *

SEQUENCE LISTING

```
<160> NUMBER OF SEQ ID NOS: 5

<210> SEQ ID NO 1
<211> LENGTH: 18
<212> TYPE: PRT
<213> ORGANISM: Artificial Sequence
<220> FEATURE:
<223> OTHER INFORMATION: Synthetic peptide

<400> SEQUENCE: 1

Lys Glu Phe Lys Arg Ile Val Gln Arg Ile Lys Asp Phe Leu Arg Asn
1               5                   10                  15

Leu Val

<210> SEQ ID NO 2
<211> LENGTH: 24
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
```

```
<222> LOCATION: (1)..(1)
<223> OTHER INFORMATION: Xaa may be any amino acid or may be absent
<220> FEATURE:
<221> NAME/KEY: MISC_FEATURE
<222> LOCATION: (2)..(2)
<223> OTHER INFORMATION: Xaa may be any amino acid or may be absent
<220> FEATURE:
<221> NAME/KEY: MISC_FEATURE
<222> LOCATION: (6)..(6)
<223> OTHER INFORMATION: Xaa may be Lys (K) or Glu (E)
<220> FEATURE:
<221> NAME/KEY: MISC_FEATURE
<222> LOCATION: (10)..(10)
<223> OTHER INFORMATION: Xaa may be Gln (Q) or Glu (E)
<220> FEATURE:
<221> NAME/KEY: MISC_FEATURE
<222> LOCATION: (14)..(14)
<223> OTHER INFORMATION: Xaa may be Asp (D) or Arg (R)
<220> FEATURE:
<221> NAME/KEY: MISC_FEATURE
<222> LOCATION: (18)..(18)
<223> OTHER INFORMATION: Xaa may be Asn (N) or Glu (E)
<220> FEATURE:
<221> NAME/KEY: MISC_FEATURE
<222> LOCATION: (21)..(21)
<223> OTHER INFORMATION: Xaa may be any amino acid or may be absent
<220> FEATURE:
<221> NAME/KEY: MISC_FEATURE
<222> LOCATION: (22)..(22)
<223> OTHER INFORMATION: Xaa may be any amino acid or may be absent
<220> FEATURE:
<221> NAME/KEY: MISC_FEATURE
<222> LOCATION: (23)..(23)
<223> OTHER INFORMATION: Xaa may be any amino acid or may be absent
<220> FEATURE:
<221> NAME/KEY: MISC_FEATURE
<222> LOCATION: (24)..(24)
<223> OTHER INFORMATION: Xaa may be any amino acid or may be absent

<400> SEQUENCE: 2

Xaa Xaa Lys Glu Phe Xaa Arg Ile Val Xaa Arg Ile Lys Xaa Phe Leu
1               5                   10                  15

Arg Xaa Leu Val Xaa Xaa Xaa Xaa
            20

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (4)..(4)
<223> OTHER INFORMATION: Xaa may be a Lys (K) or Glu (E)
<220> FEATURE:
<221> NAME/KEY: MISC_FEATURE
<222> LOCATION: (8)..(8)
<223> OTHER INFORMATION: Xaa may be a Gln (Q) or Glu (E)
<220> FEATURE:
<221> NAME/KEY: MISC_FEATURE
<222> LOCATION: (12)..(12)
<223> OTHER INFORMATION: Xaa may be a Asp (D) or Arg (R)
<220> FEATURE:
<221> NAME/KEY: MISC_FEATURE
<222> LOCATION: (16)..(16)
<223> OTHER INFORMATION: Xaa may be a Asn (N) or Glu (E)

<400> SEQUENCE: 3

Lys Glu Phe Xaa Arg Ile Val Xaa Arg Ile Lys Xaa Phe Leu Arg Xaa
1               5                   10                  15

Leu Val
```

```
<210> SEQ ID NO 4
<211> LENGTH: 24
<212> TYPE: PRT
<213> ORGANISM: Artificial Sequence
<220> FEATURE:
<223> OTHER INFORMATION: Synthetic peptide

<400> SEQUENCE: 4

Ile Gly Lys Glu Phe Lys Arg Ile Val Gln Arg Ile Lys Asp Phe Leu
1               5                   10                  15

Arg Asn Leu Val Pro Arg Thr Glu
            20

<210> SEQ ID NO 5
<211> LENGTH: 24
<212> TYPE: PRT
<213> ORGANISM: Artificial Sequence
<220> FEATURE:
<223> OTHER INFORMATION: Synthetic peptide

<400> SEQUENCE: 5

Ile Gly Lys Glu Phe Lys Arg Ile Val Glu Arg Ile Lys Arg Phe Leu
1               5                   10                  15

Arg Glu Leu Val Arg Pro Leu Arg
            20
```